(12) United States Patent
Borrel

(10) Patent No.: US 10,112,618 B2
(45) Date of Patent: Oct. 30, 2018

(54) TRAFFIC POLLUTION INDICATOR

(71) Applicant: Herve Borrel, Scottsdale, AZ (US)

(72) Inventor: Herve Borrel, Scottsdale, AZ (US)

(73) Assignee: Rimalu Technologies, Inc., Scottsdale, AZ (US)

(*) Notice: Subject to any disclaimer, the term of this patent is extended or adjusted under 35 U.S.C. 154(b) by 10 days.

(21) Appl. No.: 15/148,637

(22) Filed: May 6, 2016

(65) Prior Publication Data

US 2017/0101106 A1 Apr. 13, 2017

Related U.S. Application Data

(60) Provisional application No. 62/239,940, filed on Oct. 11, 2015.

(51) Int. Cl.
*B60W 40/02* (2006.01)
*G01N 33/00* (2006.01)

(52) U.S. Cl.
CPC ......... *B60W 40/02* (2013.01); *G01N 33/0004* (2013.01)

(58) Field of Classification Search
CPC ............... B50W 40/02; G01N 33/0004; G01C 21/00–21/3697
See application file for complete search history.

(56) References Cited

U.S. PATENT DOCUMENTS

| | | | |
|---|---|---|---|
| 4,523,870 A * | 6/1985 | Spector | A61L 9/12 239/55 |
| 4,875,406 A | 10/1989 | Hotler et al. | |
| 5,217,692 A | 6/1993 | Rump et al. | |
| 5,725,425 A | 3/1998 | Rump et al. | |
| 6,104,299 A | 8/2000 | Brusseaux et al. | |
| 6,206,775 B1 | 3/2001 | Lemaitre et al. | |
| 7,603,138 B2 | 10/2009 | Zhang et al. | |
| 7,857,892 B2 | 12/2010 | Marra | |
| 7,900,501 B2 | 3/2011 | Moseley | |
| 8,171,136 B2 | 5/2012 | Petite | |

(Continued)

FOREIGN PATENT DOCUMENTS

| | | |
|---|---|---|
| CN | 20121590228 | 7/2014 |
| CN | 20142402720 | 1/2015 |

(Continued)

OTHER PUBLICATIONS

Devarakonda et al., Real-time Air Quality Monitoring Through Mobile Sensing in Metropolitan Areas, Oct. 6, 2014, http://web.archive.org/web/20141006092530/http://www.cs.uic.edu/~urbcomp2013/papers/Paper%2019_Devarakonda.pdf.*

(Continued)

*Primary Examiner* — Aaron L Troost
(74) *Attorney, Agent, or Firm* — Lightbulb IP, LLC

(57) ABSTRACT

A traffic pollution indicator mounts to an air vent of a car or other vehicle to detect pollution and present pollution information to passengers. The traffic pollution indicator includes one or more sensors for detecting pollution, one or more microcontrollers and one or more communication devices to communicate with one or more display devices. Pollution is typically detected as a change in pollution levels by the traffic pollution indicator. Various display devices or a screen of the traffic pollution indicator present sensor information, in various visual representations, to passengers.

19 Claims, 5 Drawing Sheets

(56) References Cited

U.S. PATENT DOCUMENTS

| | | | |
|---|---|---|---|
| 8,348,732 B2 | 1/2013 | Aronstam | |
| 8,515,614 B2 | 8/2013 | Bernard | |
| 8,903,646 B2 | 12/2014 | Althen et al. | |
| 9,111,240 B2 | 8/2015 | Petite | |
| 9,141,094 B2 | 9/2015 | Pariseau et al. | |
| 9,599,597 B1 * | 3/2017 | Steele | G01N 33/0004 |
| 2008/0033644 A1 | 2/2008 | Bannon | |
| 2010/0211260 A1 * | 8/2010 | De Sanctis | G07C 5/008 |
| | | | 701/31.4 |
| 2011/0251800 A1 | 10/2011 | Wilkins | |
| 2014/0031082 A1 * | 1/2014 | Zishaan | G08B 21/12 |
| | | | 455/556.1 |
| 2014/0039988 A1 | 2/2014 | Londergran | |
| 2015/0212057 A1 | 7/2015 | Darveau | |
| 2015/0331451 A1 * | 11/2015 | Shin | G06F 3/041 |
| | | | 345/173 |
| 2016/0018228 A1 * | 1/2016 | Parker | G01O 21/3623 |
| | | | 701/412 |

FOREIGN PATENT DOCUMENTS

| | | |
|---|---|---|
| CN | 20142496531 | 1/2015 |
| DE | 2000143797 | 2/2004 |
| EP | 1190879 | 3/2002 |
| FR | 20110061342 | 6/2013 |
| JP | 19980125389 | 11/1999 |
| JP | 20080146635 | 12/2009 |
| KR | 20060035066 | 10/2007 |
| KR | 20070034588 | 10/2008 |
| KR | 20070082776 | 2/2009 |
| KR | 20100131285 | 6/2012 |
| RU | 112428 | 1/2012 |
| WO | WO2001EP09783 | 8/2001 |

OTHER PUBLICATIONS

Devarakonda et al., Real-time Air Quality Monitoring Through Mobile Sensing in Metropolitan Areas, Oct. 06, 2014, http://web.archive.org/web/20141006092530/http://www.cs.uic.edu/~urbcomp2013/papers/Paper%2019_Devarakonda.pdf (Year: 2014).*

Arduino, MQ Gas sensors, Sep. 21, 2014, https://web.archive.org/web/20140921050325/http://playground.arduino.cc/Main/MQGasSensors (Year: 2014).* codebender's blog, How to use MQ2 Gas Sensor, Jul. 19, 2015, http://blog.codebender.cc/2015/07/19/tutorial-how-to-use-mq2-gas-sensor/ (Year: 2015).*

Karin Tuxen-Bettman, Making the invisible visible by mapping air quality, Google Green Blog, Sep. 2015, http://googlegreenblog.blogspot.com/2015/09/making-invisible-visible-by-mapping-air.html (retrieved May 23, 2016).

* cited by examiner

TRAFFIC POLLUTION INDICATOR

CROSS-REFERENCE TO RELATED APPLICATION

This application claims priority to U.S. Provisional Patent Application No. 62/239,940, filed Oct. 11, 2015.

BACKGROUND OF THE INVENTION

Field of the Invention

The invention relates to traffic pollution and in particular to systems and methods for a traffic pollution indicator that senses traffic pollution variations and communicates the information to a displaying device such as a smartphone, computer or tablet.

Related Art

Traffic pollution is typically a complex mixture of particles of various sizes, and gases. Gases present in traffic pollution are often categorized in, reducing gases, such as carbon monoxide (CO), volatile organic compounds (VOCs) and hydrocarbons (HCs), and oxidizing gases, such as nitrogen oxides (NOX).

Air Quality Sensors (AQS) modules have been assembled on high end European commercial automobiles since the late 1980s. These AQS modules are now used on a large number of mid-range European and Asian car models. AQS modules are sold by several European and Asian companies to tier one automotive suppliers or OEMs for factory installation during car assembly. They are usually installed outside the cabin, close to a cabin air intake, or even around the front bumper area. They are often based on dual sensors. One sensor detects the reducing gases (VOCs HCs etc.) and the other one detects the oxidizing gases (NOX etc. . . . ). These AQS modules communicate with the car air conditioning (AC) system and issue recommendations to the AC processor to close the recirculation flap when the pollution is high, to keep the polluted air outside the cabin. When the air pollution decreases, an AQS module recommends the AC system to reopen the flap, to let some fresh air into the cabin. No indication is however usually given to the user as to when the flap is opened or closed.

Use of semiconductor gas sensors, such as AQS modules, in vehicles has been documented. For instance, the following references describe various assemblages of sensors, pollution detection, automotive air quality, and sensor signal algorithms.

European Patent Application No. EP1190879 describes an algorithm directed to outputting a flap position signal (open or close).

U.S. Pat. No. 5,217,692 describes a dual gas sensor arrangement.

U.S. Pat. No. 6,206,775 describes automotive AC with pollution sensor.

U.S. Pat. No. 7,857,892 describes pollution sensor with ultra fine particle detector.

U.S. Pat. No. 4,875,406 describes device for detecting different pollutants in gas streams.

U.S. Pat. No. 5,725,425 describes sensor system for controlling ventilation systems in vehicles.

U.S. Pat. No. 9,141,094 describes a personal air quality monitoring system focusing on particles.

U.S. Pat. No. 7,900,501 describes a multi sensor air quality monitor.

U.S. Patent Publication No. 2015/212057 describes a wearable digital air quality monitor.

Chinese Patent Application No. CN20142496531 describes an in-car air pollution monitoring device.

In general, AQS modules are useful to decrease the average pollution inside the cabin, but are less effective when the traffic pollution level is high for a prolonged period of time, as some external air has to enter the cabin to keep the level of CO2 exhaled by the passengers from building up inside the cabin.

From the discussion that follows, it will become apparent that the present invention addresses the deficiencies associated with the prior art while providing numerous additional advantages and benefits not contemplated or possible with prior art constructions.

SUMMARY OF THE INVENTION

A traffic pollution indicator is disclosed herein. The traffic pollution indicator may be a stand alone in-cabin pollution sensor unit for vehicles that provides real time traffic pollution information to passengers. The traffic pollution indicator is advantageous in that it provides useful and interesting information to users regarding the surrounding environment. In addition, the traffic pollution indicator will typically be low cost, easy to use and be compatible with a wide range of external devices, as will be described further below. Also, professional users such as law enforcement or air quality institutions may use the traffic pollution indicator to identify individual or groups of highly polluting vehicles.

Various embodiments of the traffic pollution indicator are disclosed herein. In one exemplary embodiment, a traffic pollution indicator for a vehicle is disclosed, with such traffic pollution indicator comprising one or more sensors that detect a change in concentration of one or more first types of pollution and output first sensor information based on the change in concentration of the first types of pollution, and a change in concentration of one or more second types of pollution and output second sensor information based on the change in concentration of the second types of pollution. A microcontroller receives the first sensor information and the second sensor information and generates a digital representation of the first sensor information and the second sensor information.

An enclosure is provided to house at least the microcontroller. A mount is attached to the enclosure. The mount comprises one or more air vent engagement elements for attaching the enclosure to an air vent of the vehicle. The one or more air vent engagement elements may be jaws biased to a closed position.

A wireless communication device transmits the digital representation to a display device. The display device comprises a screen, and receives the digital representation from the wireless communication device and presents a visual representation of the digital representation on the screen. The display device may be a computing device selected from the group consisting of smartphones, computers, and tablets. An alert may be outputted at the display device when the change in concentration of the first type of pollution or the change in concentration of the second type of pollution exceeds a predefined or calculated threshold.

In addition, a power cable may extend from the enclosure. A storage device may be housed in the enclosure and store the digital representation. One or more additional sensors may be provided to detect additional sensor information including temperate, humidity and particulate concentration information.

In another exemplary embodiment, a traffic pollution indicator for a vehicle comprises one or more sensors that detect pollution and output sensor information based on the same, a microcontroller that receives the sensor information and generates a digital representation of the sensor information, and a screen that presents a visual representation of the digital representation. The one or more sensors may detect pollution by detecting a change in concentration of one or more gases.

An enclosure is provided to house various components of the traffic pollution indicator. A mount is attached to the enclosure and comprising one or more engagement elements that attach to an interior portion of the vehicle. The one or more engagement elements may be jaws biased to a closed position.

The screen may be part of a display device provided with the traffic pollution indicator or by a user or third party. The visual representation may include one or more pollution graphs. One or more additional sensors may be provided to detect additional sensor information including temperate, humidity and particulate concentration information. A storage device may be provided to store the digital representation.

Various methods related to the traffic pollution indicator are also disclosed herein. For instance, in one exemplary embodiment a method for displaying pollution information in a vehicle is disclosed, with such method comprising securing a traffic pollution indicator to an air vent of the vehicle with a mount, where the traffic pollution indicator comprises one or more sensors that detect changes in pollution concentrations and generate sensor information based on the same, and one or more microcontrollers that receive the sensor information and generate a digital representation of the sensor information. The method also includes receiving the digital representation at a display device, and presenting a visual representation of the digital representation on a screen of the display device. The traffic pollution indicator is secured such that the sensors are oriented to face the air vent.

The visual representation may be generated by converting the digital representation into one or more pollution graphs. The digital representation may be received via wireless communication. In addition, it is contemplated that sensor information may only be generated when a change in pollution concentration exceeds a predefined or calculated threshold. An alert may be outputted when a change in pollution concentration exceeds a predefined or calculated threshold.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

A better understanding of the pollution entering a car or truck (or even a bike or other vehicle), can be interesting and useful to passengers, whether they have an AQS module in their car or not. There is currently no low cost commercially available system to monitor traffic pollution and provide real time information to a user.

In one or more embodiments, the traffic pollution indicator provides pollution information identifying pollution in surrounding traffic around a car. In addition or alternatively, pollution information may include identification of individual highly polluting vehicles in traffic as detected by the traffic pollution indicator. The traffic pollution indicator also displays or facilitates display of such pollution information to enable a user to identify pollution, individual polluting vehicles, or both. As such, a traffic pollution indicator may be used by end users, air quality institutions, law enforcement units, or emission compliance services.

Figure 1:
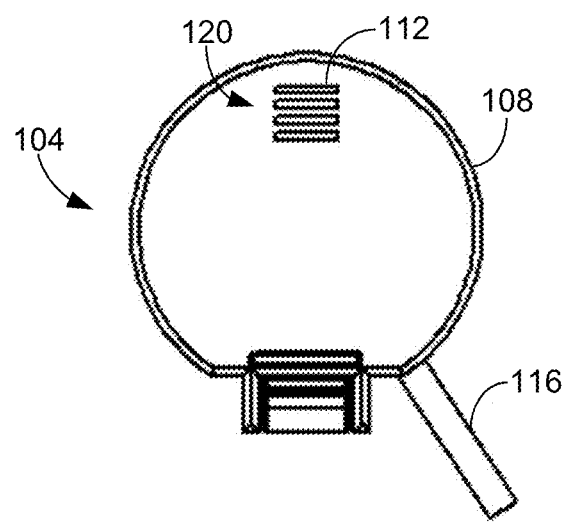
FIG. 1 is a front view of an exemplary traffic pollution indicator.

A traffic pollution indicator will now be described with regard to FIGS. 1-3. As can be seen, a traffic pollution indicator 104 may comprise an enclosure 108 that houses and protects components therein. For instance, in one or more embodiments, an enclosure 108 may be a rigid structure that contains a printed circuit board with one or more sensors, one or more microcontrollers, other electronic components, or various combinations thereof. As will be described further below, various types of sensors may be used, including dual semiconductor gas sensors.

An enclosure may comprise one or more openings 112 that expose the traffic pollution indicator's sensors in contact with surrounding air, such as air emitted from a car air vent. It is noted that an air filter 120 that captures dust and reduces or eliminates air turbulence may be between an opening 112 and sensitive elements of a sensor to facilitate accurate and reliable sensor readings. It is noted that the actual shape of the enclosure 108 may vary. In one or more embodiments, the enclosure may be smaller than half the size of a pack of cigarettes. Typically, and as will be described further below, a traffic pollution indicator 104 will be oriented such that an opening 112 faces the air flow from an air vent when the traffic pollution indicator is attached to the air vent.

A traffic pollution indicator 104 may be powered in various ways. As shown in FIG. 1 for example, a power cable 116 may provide power to the traffic pollution indicator. For example, a power cable 116 may attach a traffic pollution indicator 104 to a cigarette lighter or other power source, via an appropriate plug. It is contemplated that a power cable 116 may be various lengths and may be retractable, replaceable or permanently attached. In some embodiments, one or more batteries may power a traffic pollution indicator 104. If the batteries are internal, they may be stored in a compartment of an enclosure 108. In addition or alternatively, one or more batteries may be external to the enclosure 108 and connected to the traffic pollution indicator 104 bay a power cable 116.

Figure 2:
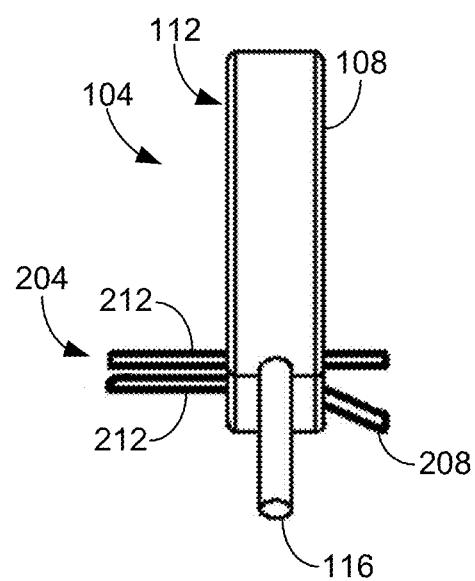
FIG. 2 is a side view of an exemplary traffic pollution indicator.
Figure 3:
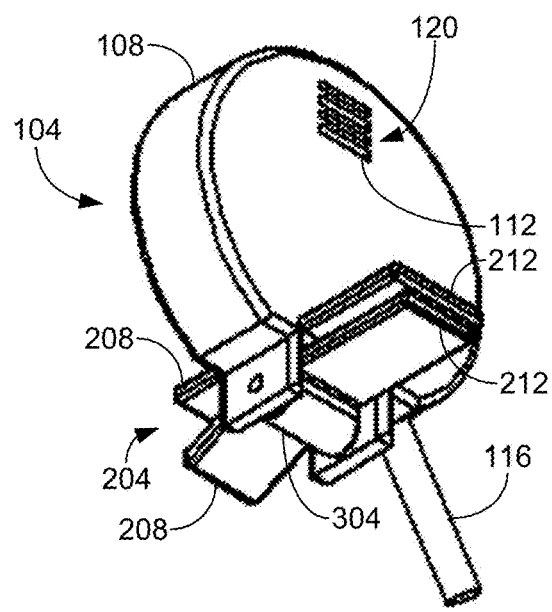
FIG. 3 is a bottom perspective view of an exemplary traffic pollution indicator.

Referring to FIGS. 2-3, an enclosure 108 will typically include a mount 204 for attaching the traffic pollution indicator to a car air vent, such as with one or more air vent engagement elements. Various types of mounts 204 may be used. As shown in FIGS. 2-3 for example, the mount 204 comprises a spring loaded clip having air vent engagement elements formed as jaws 212 used to attach a traffic pollution indicator 104 to one or more of the fins of an air vent, such as an air vent at a car dashboard. In this embodiment, the jaws 212 of the mount 204 grasp or clamp a fin of the air vent. A lever 208, button, handle or the like may be used to operate (open) the jaws 212, such as when moved or otherwise engaged by a user.

In some embodiments, one of the jaws 212 may be part of the enclosure 108 and therefore be immovable, while the other jaw is attached to a hinge 304 or pivot to allow it to move between an open and closed position relative to the first jaw. Typically, one or more of the jaws 212 will be biased to a closed position, such as by a spring or other biasing device. In one or more embodiments, a spring-loaded hinge or pivot may be used to achieve such biasing. In the embodiment of FIG. 3 for example, the hinge 304 comprises an internal spring to bias the jaws 212 to a closed position. It is contemplated that other mechanisms may be used to secure a mount 204 to an air vent, such as one or more clamps, screws, suction cups, magnets, adhesives or various combinations thereof.

Figure 4:
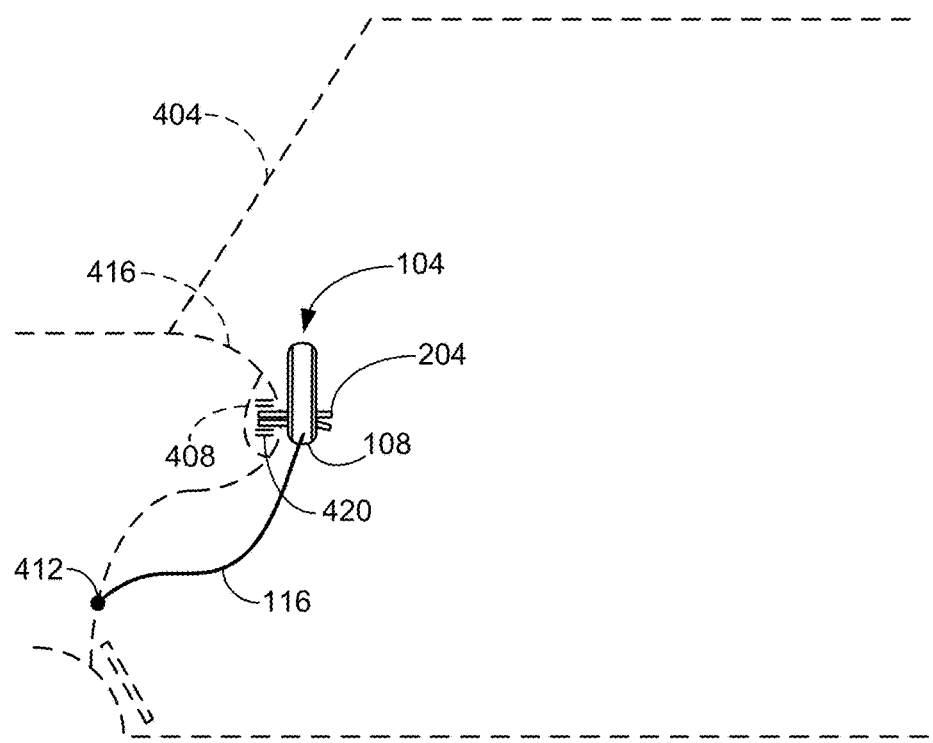
FIG. 4 is a side view of an exemplary traffic pollution indicator installed at an air vent.

FIG. 4 illustrates an exemplary traffic pollution indicator 104 installed at an air vent 408 of a car 404. FIG. 4 shows a cross section of a front passenger compartment of a car 404. Though illustrated at a dashboard 416 air vent 408 of a car 404, it is contemplated that the traffic pollution indicator 104 may be attached to various air vents of various vehicles. As can be seen, the traffic pollution indicator 104 may be clipped or otherwise mounted to an air vent 408 via one or more mounts 204. In one or more embodiments, a mount 204 may clip or clamp to or grasp one or more fins 420 of an air vent 408, such as shown in FIG. 4.

Typically, a traffic pollution indicator, when mounted, is oriented in a way that exposes one or more of its openings 112 and sensors to an incoming air flow. To illustrate, in FIG. 4, the traffic pollution indicator's opening 112 faces the air vent 408 of the car 404.

As described above, a cable 116 may connect a traffic pollution indicator 104 to a power source, such as a cigarette lighter 412, to power the traffic pollution indicator. One or more data connections may be utilized by the traffic pollution indicator 104 as well. For example, a data cable or wireless connection may be used to transmit information from a traffic pollution indicator 104 to a display device 420, such as a smartphone, computer or tablet. As will be described further below, the display device 420 will typically at least be used to display sensor information captured by a traffic pollution indicator 104 so that a user may view and make use of the same.

It is noted that a single cable may be used to carry both power and data (e.g., USB). In such case, it is contemplated that information may be transmitted to a vehicle via a cable 116, and the vehicle may transmit the information to a display device via the vehicle's communication device. For example, sensor information may be transmitted from a traffic pollution indicator 104 to a vehicle via a USB cable 116, and the vehicle may transmit the sensor information to a display device via a BLUETOOTH or other wireless (or wired) connection.

Figure 5:
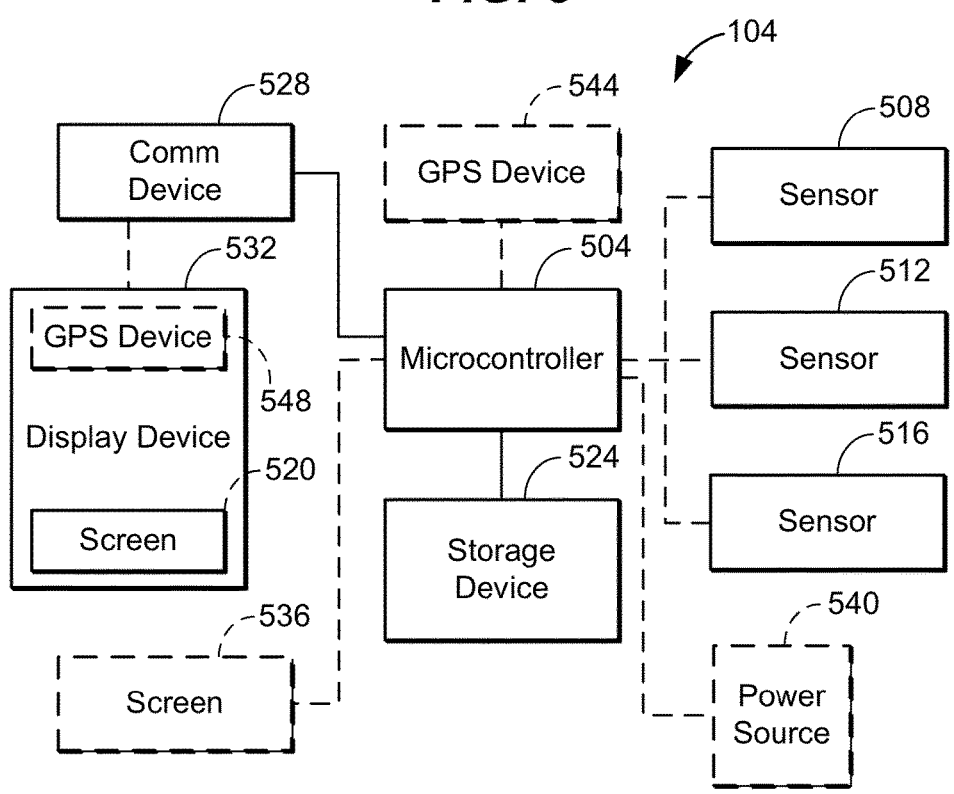
FIG. 5 is a block diagram illustrating components of an exemplary traffic pollution indicator.

Components of the traffic pollution indicator 104 will now be described with regard to FIG. 5. As can be seen, a traffic pollution indicator 104 may comprise one or more sensors 508, 512, 516. Sensors 508, 512, 516 may be individually sensitive to one or more traffic pollutants, such as carbon monoxide (CO), a broad set of hydrocarbons (HC), volatile organic compounds (VOCS), and nitrogen oxides (NOX). In addition, one or more sensors 508, 512, 516 may detect a wider range of pollutants, such as for example, gases of the ammonia family. Alternatively, specialized sensors 508, 512, 516 that each are sensitive to a distinct set of pollutants may be used. As disclosed above, sensors will typically be positioned adjacent an opening of a traffic pollution indicator's enclosure to permit exposure to air coming into a vehicle.

In one exemplary embodiment, a sensor 508, 512, 516 may perform its gas or pollution sensing function via a change of conductivity at a metal oxide or other sensing material that is brought to a temperature between one hundred and five hundred degrees centigrade. The temperature may be selected based on the type of sensing material used and the gases to detect. The gases present in the air contact the surface of the sensing material, and create changes in conductivity. This sensor information (i.e., the conductivity variations) may be converted to digital signals using standard electronics, such as analog to digital converters.

It is noted that, in some embodiments, the sensors 508, 512, 516 of a traffic pollution indicator may not be calibrated or compensated for temperature or humidity variations. In addition, the sensors may react to a wide range of gases. The traffic pollution indicator accordingly may not output any information regarding any specific absolute gas concentration. Similar to a traditional automotive AQS module, a traffic pollution indicator may provide information on relative changes in aggregate gas concentration (i.e., pollution). In embodiments with multiple sensors 508, 512, 516 or individual sensors capable of discerning between different gas/pollution concentrations, the traffic pollution indicator may differentiate between reducing and oxidizing gas pollutants. This is basically the difference between mainly gasoline vehicle pollution (reducing), and mainly diesel vehicle pollution (oxidizing). Differentiation between other types of pollutants may also be detected by using sensors 508, 512, 516 with various sensing capabilities.

In other embodiments, the traffic pollution indicator includes temperature and humidity compensations to improve quality of the pollution event detection or even allow the software to extract information on absolute levels of surrounding pollution. For example, one or more temperature, humidity, or particulate concentration sensors may be included in a traffic pollution indicator to gather readings related to the same in the air. This additional sensor information may then be used to compensate for temperature, humidity or other shortcomings of AQS or other sensors.

A traffic pollution indicator 104 will typically also include one or more processors or microcontrollers 504. A microcontroller 504 may execute machine readable code comprising instructions to cause a traffic pollution indicator 104 to function as disclosed herein. For example, and as will be described further below, machine readable code may cause a traffic pollution indicator 104 to receive sensor information from one or more sensors 508, 512, 516 to extract information about pollution variations in the environment, such as around or ahead of a car. Machine readable code may also include instructions to process, format and display sensor information, or various combinations thereof.

A microcontroller 504 may also include various hardware components. For example, a microcontroller 504 may include one or more analog to digital converters to convert any analog signals from a sensor to a digital signal for processing by the microcontroller.

It is noted that machine readable code may be stored in one or more storage devices 524 or hardwired in a microcontroller 504 itself. Though shown as external to the microcontroller 504 in FIG. 5, it is contemplated that a storage device 524 may be internal to a microcontroller in one or more embodiments. In addition or alternatively to machine readable code, a storage device 524 may store various information, including sensor information from one or more sensors 508, 512, 516.

The traffic pollution indicator 104 includes a wireless function to communicate with a display device 532 in a vehicle, such as a smartphone, computer or tablet having a screen 520 to present information from the traffic pollution indicator. As shown in FIG. 5 for instance, one or more communications devices 528 may be provided to communicate with an external display device 532 via a wired or wireless connection. Some exemplary communication devices 528 include cellular transceivers, BLUETOOTH transceivers, WiFi transceivers, USB ports, and the like. A display device may also or alternatively be an onboard computer or computing device of a vehicle having a screen, such as an entertainment or information system of the vehicle.

It is contemplated that a display device 532 need not be provided with a traffic pollution indicator 104 in some embodiments. In such case, the traffic pollution indicator 104 may display sensor information on its own screen 536, and a separate display device 532 may, but need not, be used in addition or instead of the screen.

It is contemplated that a traffic pollution indicator 104 may optionally include a location detection device 544, such as a GPS device. A location detection device 544 would be used to determine the location of the traffic pollution indicator 104 so that particular sensor information can be associated with a location. For example, the determined location may be transmitted along with sensor information for subsequent display and/or storage at a display device or storage at a storage device. Typically, a location detection device 548 of a display device 532 will be used to provide location information. In such case, the display device 532 may associate sensor information with location information.

An internal power source 540, such as one or more batteries or solar panels, may optionally be included as well. As discussed above, a traffic pollution indicator 104 may be powered by an external power source, such as vehicle power, in addition or instead of an internal power source.

Generally, when in operation, a traffic pollution indicator 104 converts analog sensor information into digital values, processes the sensor information to extract information that can be displayed to a user, and communicates with a display device that presents information to the user. Optionally, a display device 532 may perform such conversion, processing or both. In such embodiments, sensor information would be transmitted from a traffic pollution indicator 104 to the display device 532 for conversion, processing or both by a processor of the display device.

In one embodiment, a traffic pollution indicator may continuously monitor two aggregate pollution variations (e.g., reducing gases and oxidizing gases). As a car carrying the traffic pollution indicator is driven in traffic, the traffic pollution indicator senses the pollutants in the air entering the cabin through the air vents. It therefore detects the pollution generated by the vehicles in traffic ahead of it. In general, a traffic pollution indicator will clearly detect a vehicle with highly polluting emissions, driving in front of it, at a distance ranging from a few meters to approximately one hundred meters.

Detection efficiency and distance depends typically mainly on the speed of the vehicles, wind speed, and the background pollution level. For example, with a strong lateral wind, the detection of pollutants will not be as clear, since the concentration of pollutants entering the cabin will be lower. At a higher vehicle speed, the detection distance can be larger since the gases have less time to disperse before they reach the air vents. Also, the same highly polluting vehicle will also be less predictably detected if it is in dense traffic with relatively high background pollution, than if it is an isolated vehicle on an empty road.

A traffic pollution indicator also may include a software application, that can be downloaded and installed on a variety of display devices to communicate wirelessly with the traffic pollution indicator. It is contemplated that the software application may also be executable on the traffic pollution indicator, such as by its microcontroller. The software application may be stored on a storage device of the traffic pollution indicator, on data storage media, a remote server or the like for retrieval and installation by a display device.

In general, this software application facilitates communication of sensor information (or other information) between the traffic pollution indicator and a display device, and display of information related to pollution detected by the traffic pollution indicator. In one or more embodiments, the information displayed may describe the amplitude and speed of the pollution variations, and the type of pollution, such as whether the pollution is mainly gasoline or diesel or a combination of both. Pollution variation graphs can also be generated by the software application and displayed to the user on a display device to provide finer information about pollution variations.

Figure 6:
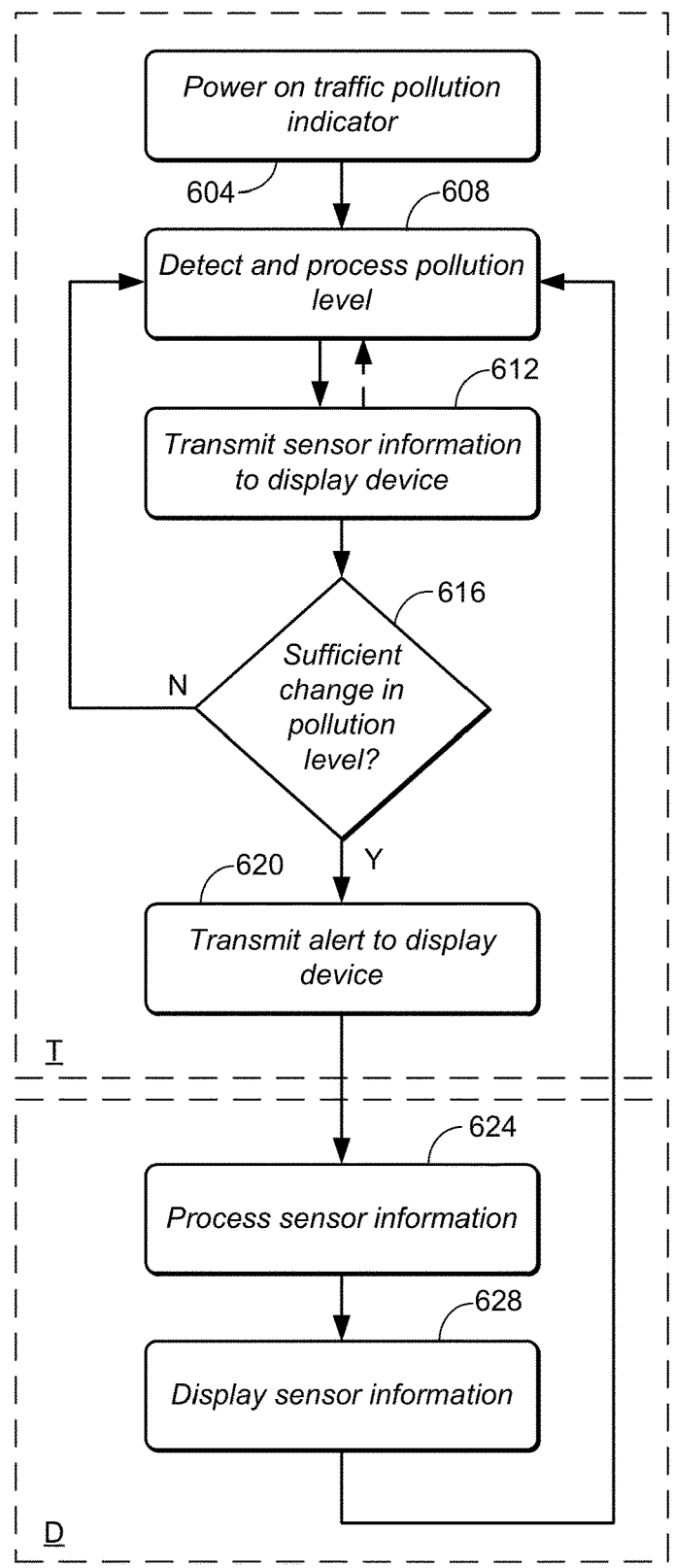
FIG. 6 is a flow diagram illustration operation of an exemplary traffic pollution indicator.

Operation of the traffic pollution indicator will now be described with regard to the flow diagram of FIG. 6. At a step 604, the traffic pollution indicator is powered on. At a step 608, one or more sensors may be activated and begin detecting pollution levels (i.e., gas concentrations). This sensor information generated by the sensors may be transmitted to a microcontroller at a step 612, so that, at a decision step 616, if a sufficient change in pollution levels is detected, an alert or other notification may be transmitted to a display device at a step 620. A microcontroller may process sensor information it receives at step 608, such as by converting analog sensor information into a digital representation thereof.

In some embodiments, the change in pollution level may have to be beyond a predefined threshold to be deemed a sufficient change at decision step 616. If not, the sensors may continue detecting pollution levels at step 608. It is noted that, in some embodiments, sensor information may continuously be transmitted to a display device regardless of whether a change is detected, such as indicated by the broken line arrow from step 612 to step 608 forming a loop between the two steps.

In addition to being predefined, a threshold may also or alternatively be variable or calculated. For example, a threshold may start at a particular value and be adjusted based on pollution levels as represented in sensor information. In one or more embodiments, a threshold may be lowered if pollution levels have been stable (within a range) or low (below a particular low point) for a predefined period of time. The threshold may be raised if pollution levels are unstable or not low.

At a step 624, sensor information may be processed, such as by a display device's processor. In one or more embodiments, the display device may execute a software application to process the data. Processing of the sensor information generally results in a graph or other visual representation based on raw sensor information. For example, pollution levels in the sensor information may be plotted on a graph, displayed as a number or color. At a step 628, the visual representation may be displayed on a screen or the like of the display device. This process may repeat, as indicated by the process returning to step 608 to detect pollution levels once a particular set of sensor information has been displayed at step 628.

As described above, in some embodiments, various operations may be shared between a traffic pollution indicator and a display device. FIG. 6 provides dashed boxes labeled "T" and "D" that respectively separate operations performed by a traffic pollution indicator and a display device. The separation of operations may vary for different embodiments of the traffic pollution indicator. As stated, in some embodiments, a traffic pollution indicator may perform all of the operations and, in such case, an external display device would not be required.

Figure 7:
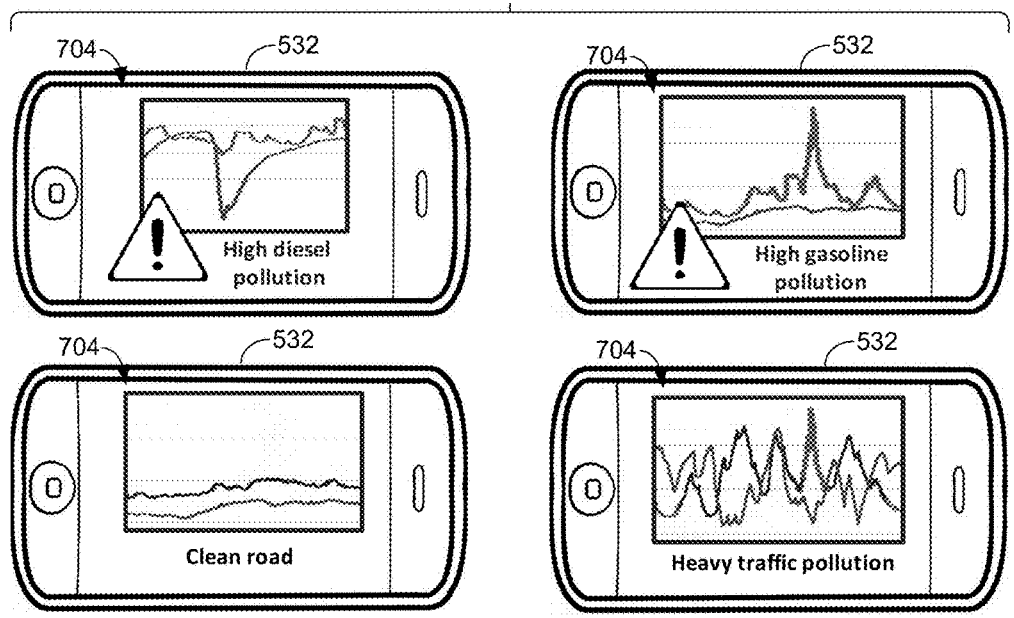
FIG. 7 illustrates exemplary display devices displaying sensor information.

FIG. 7 illustrates a set of visual representations of sensor information presented on a screen of a display device. The graph labeled "High Diesel Pollution" indicates a sharp increase in diesel pollution while the gasoline pollution remains relatively stable. The graph labeled "High Gasoline Pollution" indicates a sharp increase in gasoline pollution while the diesel pollution remains relatively stable. The graph labeled "Clean Road" indicates a low level of both types of pollution as indicated by the relative calm in the lines representing gasoline and diesel pollution. The graph labeled "Heavy Traffic Pollution" shows multiple changes in both types of pollution as indicated by spikes in both lines of the graph.

In one embodiment of the invention, the traffic pollution indicator provides information that allows a user to identify individual highly polluting vehicles. This is advantageous in helping to reduce overall traffic pollution, as it is known that a small percentage of highly polluting vehicles are responsible for a significant portion of overall traffic pollution. Law enforcement units can therefore use the traffic pollution indicator to stop a suspected vehicle and control its smog check status.

To illustrate, after a first high pollution signal is detected by the traffic pollution indicator (like that shown in the "High Diesel Pollution" and "Gross Gasoline Polluter" graphs of FIG. 7), a law enforcement vehicle may follow the suspected vehicle to confirm such detection. One of the goals is to eliminate the possibility that another highly polluting vehicle in front of the suspected one is creating most of the pollution. This may be accomplished by following the suspected vehicle for a predefined period, such as a minute or more (ideally with several stops and starts, as it is when a vehicle is set in motion or strongly accelerates that it releases the most pollution). In this mode of the traffic pollution indicator, all user displays and messages are directed to individual vehicle identification instead of general information about traffic pollution.

One or more alerts may be presented or otherwise outputted by a display device upon occurrence of one or more triggering events. An exemplary alert is illustrated in the "High Diesel Pollution" graph of FIG. 7. A triggering event may be defined as a change in pollution level of an amplitude beyond a predefined or calculated threshold. To illustrate, the "High Diesel Pollution" and "Gross Gasoline Polluter" graphs show a change respectively in diesel pollution, while the gasoline pollution remains more stable, and a change in gasoline pollution, while the diesel pollution remains more stable. The two measures will typically be mainly independent. If one measure of pollution "spikes" beyond a predefined or calculated threshold, it is contemplated that an alert may be generated. It is noted that a traffic pollution indicator may include one or more speakers, lights or other output devices to output an alert.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A traffic pollution indicator for a vehicle comprising:
one or more uncalibrated sensors that output a signal varying with time, representing variations in an aggregate concentration of gases with time of one or more types of pollution, without carrying at any time any information on any absolute gas concentration;
a microcontroller that receives the signal and generates a digital representation of the signal;
a wireless communication device that transmits the digital representation to a display device;
an enclosure housing at least the microcontroller; and
a mount attached to the enclosure and comprising one or more air vent engagement elements for attaching the enclosure to an air vent of the vehicle;
wherein the display device comprises a screen and receives the digital representation from the wireless communication device and presents a visual representation of the digital representation on the screen;
wherein the signal is only generated when at least one of the variations in the aggregate concentration exceeds a predefined or calculated threshold.

2. The traffic pollution indicator of claim 1, wherein the display device is a computing device selected from the group consisting of smartphones, computers, tablets, and vehicle entertainment systems.

3. The traffic pollution indicator of claim 1 further comprising a power cable extending from the enclosure.

4. The traffic pollution indicator of claim 1 further comprising one or more additional sensors that detect additional sensor information selected from the group consisting of temperature, humidity and particulate concentration information.

5. The traffic pollution indicator of claim 1 further comprising a storage device housed in the enclosure, wherein the storage device stores the digital representation.

6. The traffic pollution indicator of claim 1, wherein the display device outputs an alert when at least one of the variations in the aggregate concentration exceeds a predefined or calculated threshold.

7. The traffic pollution indicator of claim 1, wherein the one or more air vent engagement elements are jaws biased toward a closed position with a biasing device.

8. The traffic pollution indicator of claim 1 further comprising an additional screen that presents the visual representation of the digital representation, wherein the additional screen is housed in the enclosure.

9. The traffic pollution indicator of claim 1, further comprising an audio output device that emits an alert when at least one of the variations in the aggregate concentration exceeds a predefined or calculated threshold.

10. The traffic pollution indicator of claim 1, wherein the visual representation includes one or more pollution graphs.

11. The traffic pollution indicator of claim 1 further comprising a power source housed within the enclosure.

12. The traffic pollution indicator of claim 1, wherein the display device executes machine readable code fixed on a non-transient storage medium to generate the visual representation.

13. The traffic pollution indicator of claim 1, wherein the screen identifies individual highly polluting vehicles in traffic by displaying an alert indicating the same when at least one of the variations in the aggregate concentration are of a particular amplitude.

14. The traffic pollution indicator of claim 13, wherein the screen also presents instructions to follow a vehicle along with the alert.

15. A method for displaying pollution information in a vehicle comprising:
    securing a traffic pollution indicator to an air vent of the vehicle with a mount, the traffic pollution indicator comprising one or more uncalibrated sensors that output sensor information comprising a signal varying with time, representing variations in an aggregate concentration of gases with time of one or more types of pollution, without carrying at any time any information on any absolute gas concentration, and one or more microcontrollers that receive the sensor information and generate a digital representation of the sensor information;
    receiving the digital representation at a display device; and
    presenting a visual representation of the digital representation on a screen of the display device;
    wherein the sensor information is only generated when at least one of the variations in the aggregate concentration exceeds a predefined or calculated threshold.

16. The method of claim 15 further comprising generating the visual representation by converting the digital representation into one or more pollution graphs.

17. The method of claim 15, wherein the digital representation is received via wireless communication.

18. The method of claim 15, wherein the traffic pollution indicator is secured such that the one or more sensors are oriented to face the air vent.

19. The method of claim 15 further comprising outputting an alert when at least one of the variations in the aggregate concentration exceed a predefined or calculated threshold.

* * * * *